United States Patent
Tu et al.

Patent Number: 6,016,437
Date of Patent: Jan. 18, 2000

[54] CATHETER PROBE SYSTEM WITH INFLATABLE SOFT SHAFTS

[75] Inventors: Hosheng Tu, Tustin; Chi-Wu James Chang, Cerritos, both of Calif.

[73] Assignee: Irvine Biomedical, Inc., Irvine, Calif.

[21] Appl. No.: 09/138,455

[22] Filed: Aug. 21, 1998

Related U.S. Application Data

[63] Continuation-in-part of application No. 08/735,199, Oct. 21, 1996.

[51] Int. Cl.[7] ........................................................ A61B 5/04
[52] U.S. Cl. ............................. 600/374; 606/41; 604/96; 607/122
[58] Field of Search .................................... 607/116, 119, 607/122; 600/139, 140, 143, 152, 206, 373, 374, 377, 381; 604/95, 96, 264, 523, 528, 530

[56] References Cited

U.S. PATENT DOCUMENTS

| | | | |
|---|---|---|---|
| 4,699,147 | 10/1987 | Chilson et al. | 128/642 |
| 4,940,064 | 7/1990 | Desai | 607/122 |
| 4,960,134 | 10/1990 | Webster, Jr. | 607/116 |
| 5,255,679 | 10/1993 | Imran | 128/642 |
| 5,313,943 | 5/1994 | Houser et al. | 128/642 |
| 5,345,936 | 9/1994 | Pomeranz et al. | 128/642 |
| 5,409,000 | 4/1995 | Imran | 128/642 |
| 5,411,025 | 5/1995 | Webster, Jr. | 128/642 |
| 5,555,883 | 9/1996 | Avitall | 128/642 |
| 5,628,313 | 5/1997 | Webster, Jr. | 128/642 |
| 5,891,027 | 4/1999 | Tu et al. | 600/374 |

*Primary Examiner*—Linda C. M. Dvorak
*Assistant Examiner*—David Ruddy

[57] ABSTRACT

A cardiovascular catheter probe system suitable for electrophysiology mapping and radiofrequency ablation of cardiac tissue comprises a plurality of catheter shafts having a proximal end, a distal handle, and a lumen extending therebetween, wherein a distal portion of the shaft is deflectable and inflatable; the wavy soft distal section is inflatable to conform intimately to the irregular intracardiac tissue surface, wherein conducting electrodes are secured on the hills of said inflatable wavy soft shaft.

2 Claims, 4 Drawing Sheets

CATHETER PROBE SYSTEM WITH INFLATABLE SOFT SHAFTS

CROSS-REFERENCE TO RELATED APPLICATIONS

This application is a continuation-in-part application of U.S. application Ser. No. 08/735,199, entitled "Cardiovascular Catheter System with an Inflatable Soft Tip", filed Oct. 21, 1996, and is incorporated herein by reference.

FIELD OF THE INVENTION

The present invention generally relates to improved constructions for cardiovascular catheters. More particularly, this invention relates to methods and apparatus for diagnosing and treating cardiac arrhythmias via a catheter probe system having one or more of the catheter shafts with a pre-shaped soft shaft section which may be inflated.

BACKGROUND OF THE INVENTION

Symptoms of abnormal heart rhythms are generally referred to as cardiac arrhythmias, with an abnormally rapid rhythm being referred to as tachycardia. The present invention is concerned with the treatment of tachycardias which are frequently caused by the presence of an "arrhythmogenic region" or "accessory atrioventricular pathway" close to the inner surface of the chambers of a heart. The heart includes a number of normal pathways which are responsible for the propagation of electrical signals from upper to lower chamber necessary for performing normal function. The presence of arrhythmogenic region or accessory pathways can bypass or short circuit the normal pathways, potentially resulting in very rapid heart contractions, referred to here as tachycardias.

Cardiac mapping is used to locate aberrant electrical pathways and currents emanating within the heart. The aberrant pathways cause the contractions of the heart muscle to take on abnormal and life threatening dysrhythmias. Intracardiac mapping requires careful positioning of a plurality of catheters of multiple electrodes within the heart. For example, Webster, Jr. U.S. Pat No. 4,960,134 show the general use of a catheter, Desai U.S. Pat. No. 4,940,064 show the use of generally planar mapping arrays, Chilson U.S. Pat. No. 4,699,147 shows the use of a three dimensional basket mapping array, Houser U.S. Pat. No. 5,313,943 shows the use of a fluid flow conduit, and Imran U.S. Pat. No. 5,409,000 shows the use of ultrasonic markers of a basket array. Other catheter probes with a basket array include U.S. Pat. Nos. 5,255,679, 5,345,936, 5,411,025, and 5,628,313. It is important for a catheter or a catheter system to intimately contact the tissue for effective and time-saving mappings with minimum fluoroscopic exposure.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a clinician to be able to accurately steer the catheter to the region for ablation. Once at the region, it is important for a catheter to intimately contact the tissue to effectively control the emission of energy to ablate the tissue within the heart.

Regardless of the type of mapping means or ablation means used, the clinician is called upon to remotely move and manipulate the catheters in various ways. First, a catheter is inserted into a major vein or artery, usually in the neck or groin area. It is then guided into chambers of the heart by appropriate manipulation through the vein or artery. The distal tip section of a catheter must be manipulatable by a user from the proximal end of the catheter, so that the electrodes at the tip section can be positioned against the tissue region at the desired location to assure that all aberrant electrical pathways are mapped.

The development of prior mapping catheters has focused upon the requirements of in vitro mapping mechanisms. It requires the tip section including the electrodes as well as the catheter shaft to form a smooth continuous curve that may not intimately contact the non-smooth intracardiac tissue. The prior development has overlooked the important need to intimately contact the tissue by the electrodes, not the inter-electrode shaft itself, especially under the circumstances of the irregular intracardiac tissue contour. The intimate contacting of the electrodes alone of a catheter shaft section via an inflatable soft shaft against the target tissue ensures effective cardiac mapping or ablation.

SUMMARY OF THE INVENTION

The present invention provides an improved cardiovascular catheter probe system which can be used in mapping and ablating the arrhythmogenic region. The improved catheter probe system provides an intimate tissue contact so that reliable mapping signals can be obtained and/or desired ablation energy can be applied effectively. In one embodiment, a catheter probe of this invention comprises a plurality of catheter shafts, each having a distal end, a proximal end, and a lumen extending therebetween, wherein a distal portion of the shaft is deflectable, and wherein at least one of the shafts comprises an inflatable wavy soft section.

The soft shaft in this invention may be made of polyethylene, polyethylene terephthalate, silicone, polyurethane, or the like material which can be formed as a thin wall tubular shaft or "balloon" and be inflated thereafter during intended clinical procedures. The thin wall tubular shaft may be either compliant such as those made of silicone and polyurethane, or non-compliant such as those made of polyethylene, polypropylene, polyether block amides (trade name Pebax®), and polyethylene terephthalate.

The pressure to inflate the soft shaft section is generally higher than the in vivo heart chamber pressure. The non-inflation pressure in this invention is defined as the pressure lower than the designated inflation pressure, such as that equal to or lower than the in vivo heart chamber pressure. The inflation fluid can be either saline or saline solution containing a contrast agent for fluoroscopy imaging. The inflatable wavy soft shaft may be pre-shaped at a simulated inflation pressure to a curvature which conforms intimately to the intracardiac surface. The catheter shaft itself possesses a relatively straight configuration under no inflation pressure. This shall render the catheter probe easy to be inserted into or discharged from the cardiovascular system. After insertion in place, the soft shaft starts to turn curvature under an inflation pressure. The shaft curvature is proportional to the inflation pressure until it reaches its pre-shaped status at a pre-determined inflation pressure. This type of curving under an inflation pressure can be achieved by a double-lumen shaft. The inflation pressure is applied to the outer lumen to force the shaft to curve conforming to the pre-shaped pattern while the inner side lumen is kept at nominal pressure. The curved shaft under an inflation pressure is resilient and can be slightly pushed from the proximal end of the catheter probe against the tissue so that all the electrodes contact intimately the tissues for mapping or ablation purposes.

In another embodiment, the improved catheter probe system has steering wires extending from the handle through the central lumen and being attached to the distal end of the shaft, having a steering mechanism. In this embodiment, the ultimate shaft curve shape of an inflatable soft shaft section of the catheter probe is controlled by the steering mechanism. However, the intimate contact between the electrodes and the tissue is assisted via the resilient shaft section under an inflation pressure.

In still another embodiment, the exterior surface of the soft shaft section is consisted of a wavy pattern. The electrodes shall be placed right on the peak of the wavy soft shaft. The electrodes are preferred to form a round surface so that the contact point of the catheter to the intracardiac tissue is through the round hill surface of the electrodes, instead of the bare inter-electrode shaft surface. The circumferential diameter of an electrode is generally larger than the tubing shaft diameter.

Signal conducting electrodes are placed on the soft shaft section while their insulated conducting wires are passed through the shaft lumen to the handle connector. The diameter of the electrode is generally larger than the shaft diameter.

In still another embodiment, a catheter probe system comprises a plurality of flexible longitudinally extending shafts each having a distal end, a proximal end, and a lumen extending therebetween, whereby an inflatable soft shaft section in one or more of the catheter shafts of a basket type catheter system. Each individual shaft of the catheter probe system has a resilient soft shaft section under an inflation pressure.

In one embodiment, a catheter of this invention has a separate inner lumen to be used for passage of conducting wires, and/or a guidewire for guiding the catheter into the blood vessel and the heart. The outer lumen having a wavy inflatable outer surface, comprising a plurality of hills and valleys, of this invention can be inflated to render electrode-to-tissue intimate contacting during clinical procedures. In this embodiment, the inflation fluid can be injected from the fluid injection port into this co-centric outer luminal space to inflate the inflatable soft shaft section. A double-lumen catheter shaft is used for this embodiment.

The catheter system may consist of two tubing sections: the distal soft inflatable shaft section and the main catheter shaft section. In order to provide increased torsional rigidity to the main catheter shaft, the main shaft material preferably comprises a polymeric tubing having a desired hardness. Preferably, the shaft has a composite structure including a base layer of a relatively low Durometer material, a stiffening layer, for example, metal braid or coil, and an outer layer comprising the biocompatible polymeric material. To enhance biocompatibility, the catheter shaft further comprises surface coating of heparin, hirudin, antibiotics, or the like on the blood or body tissue contacting surface of the catheter shaft.

A method for positioning a catheter probe system having a soft inflatable shaft section within a heart chamber comprises percutaneously introducing the distal end of a catheter probe through an aorta to the heart chamber, wherein electrodes are disposed at the distal section of the catheter probe; connecting the handle means to the catheter shaft; and inflate the distal end portion of the catheter shafts about half an atmosphere or higher above the normal in vivo chamber pressure to enable the inflated shaft section to curve or being assisted via a steering mechanism to conform to the irregular intracardiac surface. Once at the desired location, the electrical signal obtained from the tissue to the electrodes on the inflated shaft section can be transmitted to the exterior ECG monitor for cardiac mapping. Alternately, the radiofrequency energy can be applied to one or more of the electrodes on the inflated shaft section once an intimate contact with the tissue is achieved using the catheter of this invention.

The method and apparatus of the present invention have several significant advantages over known catheters. In particular, the intimate contact of electrodes against the desired intracardiac tissue by using a catheter probe system having an inflatable soft shaft section is achieved.

Figure 1:
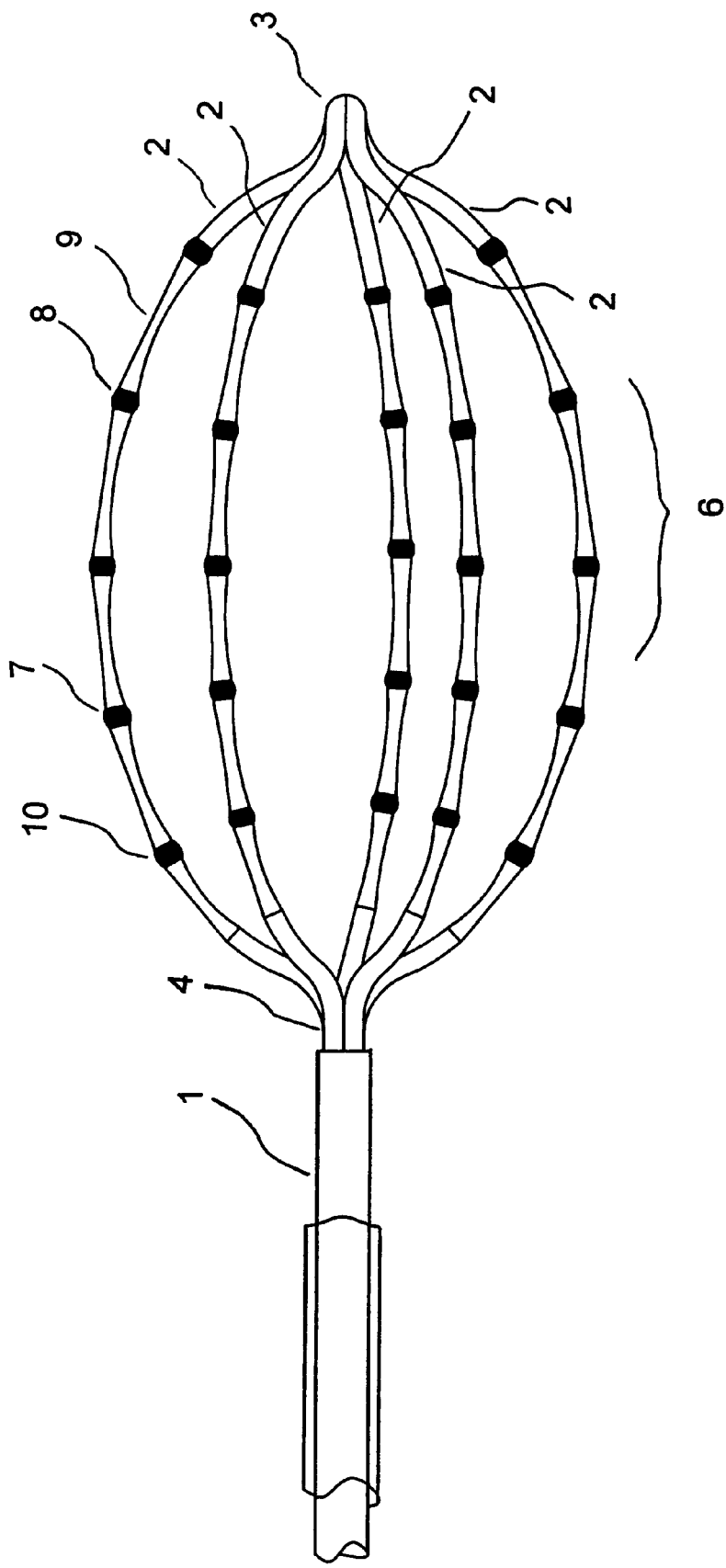
FIG. 1 is a front elevational view of the catheter probe system having a plurality of shafts and a plurality of electrodes on at least one inflatable wavy shaft constructed in accordance with the principles of the present invention.

FIG. is one of the inflatable wavy shaft of the catheter probe system of FIG. 1 under no inflation pressure.

Figure 3:
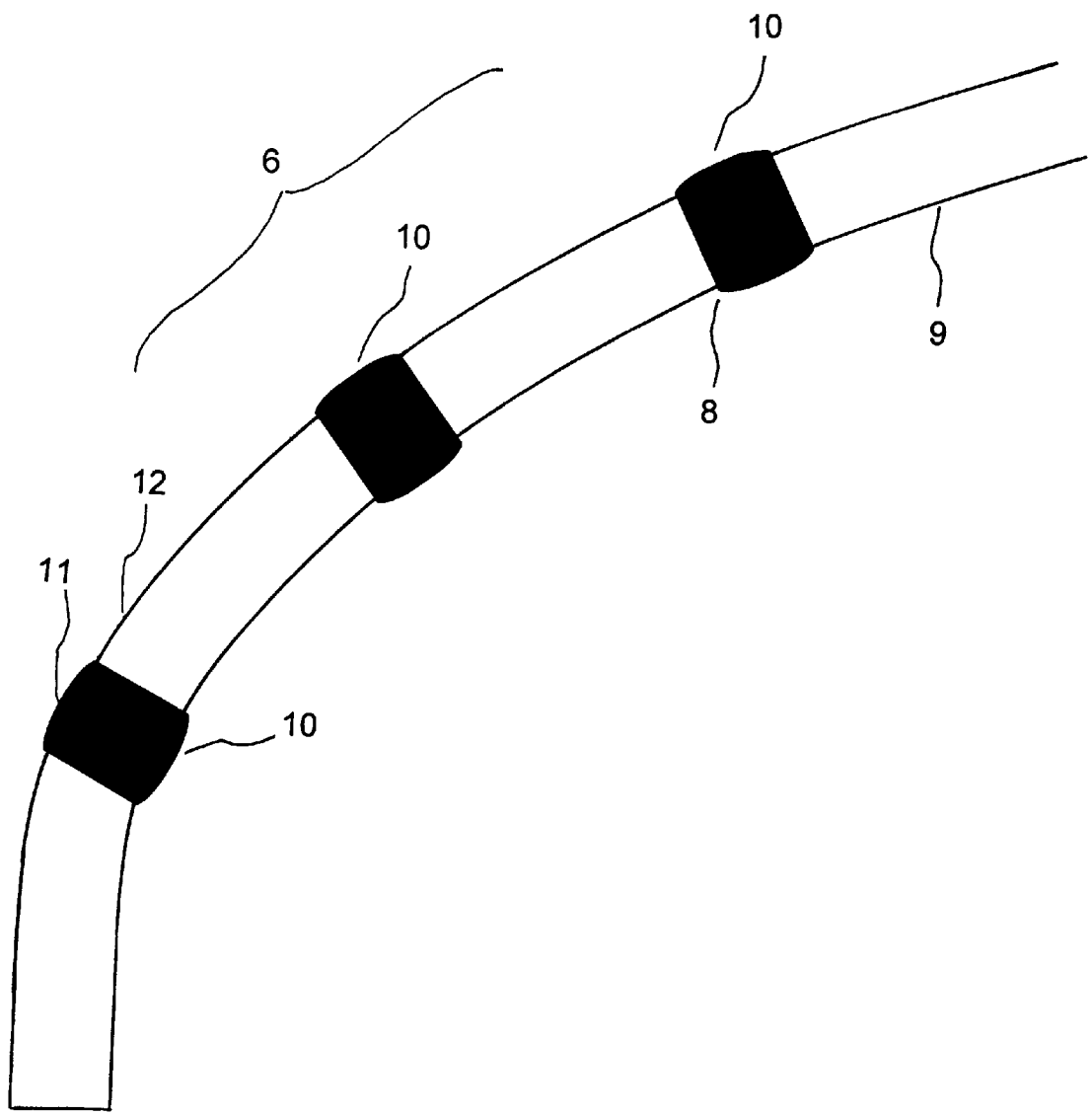

FIG. 3 is an inflatable wavy shaft of the catheter probe system under inflation pressure constructed in accordance with the principles of the present invention.

Figure 4:
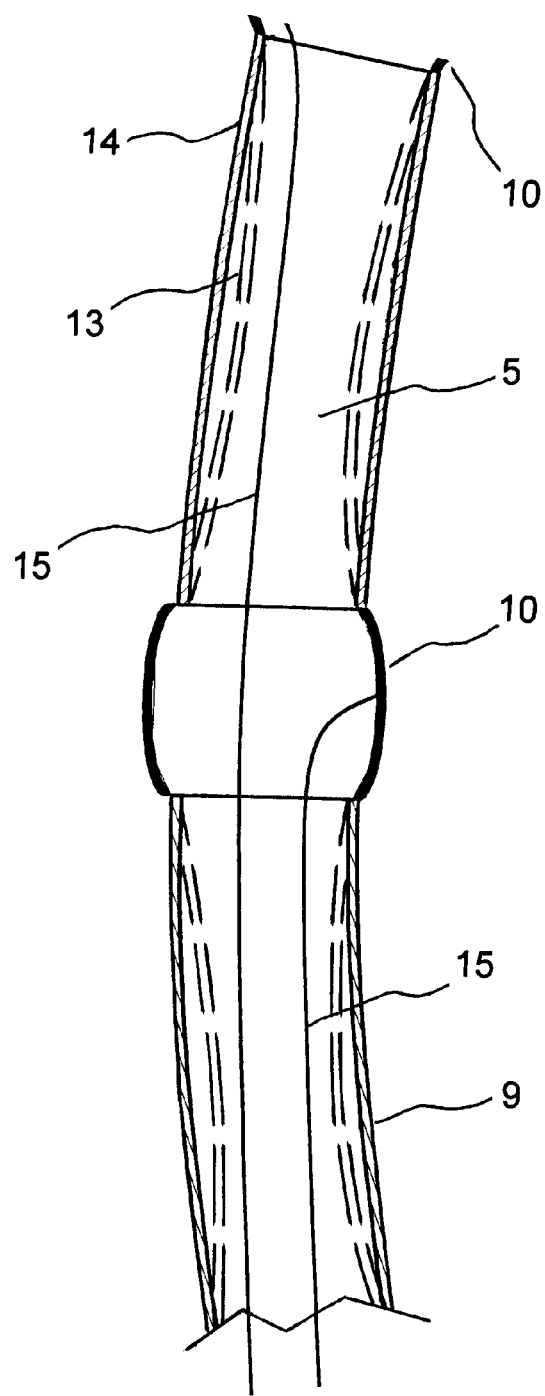

FIG. 4 is a cross-sectional view of one catheter shaft of the catheter probe system under inflation pressure.

DETAILED DESCRIPTION OF EXEMPLARY EMBODIMENTS

Referring to FIG. 1, a catheter probe system 1 constructed in accordance with the principles of the present invention comprises a plurality of flexible longitudinally extending shafts 2 each having a distal end 3, a proximal end 4, and a lumen 5 extending therebetween. At least one of the catheter shafts 2 of the catheter probe system has an inflatable wavy soft shaft section 6, wherein the outer surface 7 of said inflatable wavy soft shaft 6 has a plurality of hills 8 and valleys 9. A plurality of conducting electrodes 10 is secured on the hills 8 of said inflatable wavy soft shaft 6. There provides pressurization means for inflating the inflatable wavy soft shaft 6, wherein said inflatable wavy soft shaft is pre-shaped to form a generally straight configuration in an uninflated state and to form a curved configuration in an inflated state. Said conducting electrodes 10 individually encircle said inflatable wavy soft shaft 6 and have an outermost circumferential diameter larger than the outer diameter of the catheter shaft. Said valleys 9 have an uninflated geometry wherein the uninflated diameter of the valleys is less than said outermost circumferential diameter of the conducting electrodes 10. And said valleys 9 further have an inflated geometry wherein the inflated diameter of the valleys is less than said outermost circumferential diameter of the conducting electrodes, but greater than the uninflated diameter of the valleys 9. A conducting wire 15 is secured to each electrode 10 for signal transmission to an ECG monitor (not shown) or for radiofrequency energy transmitted from an external radiofrequency energy generator.

Figure 2:
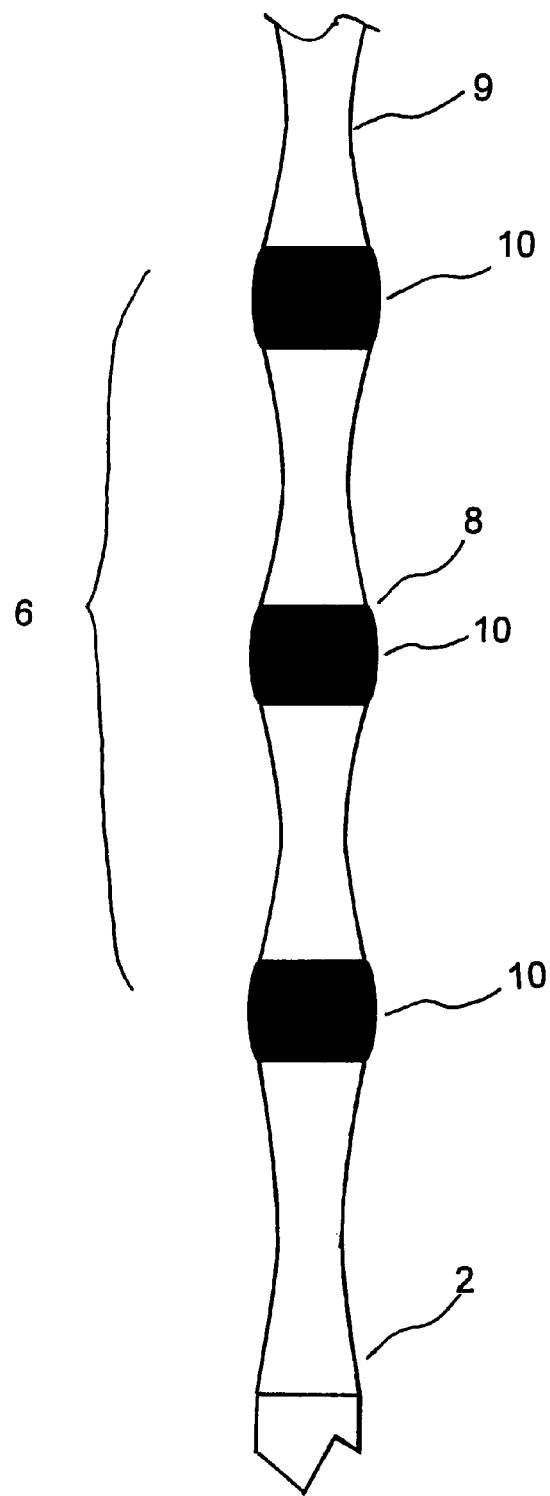

FIG. 2 shows an inflatable soft shaft 6 of FIG. 1 under no inflation pressure. It consists of a plurality of electrodes 10, wherein the electrodes are located on and adhered to the hills 8 of the wavy inflatable tubing shaft 6 of the catheter shaft 2. The shape of the outer surface of the electrodes is round. In one embodiment, the soft shaft may be reinforced internally by an inner lumen or tubing. The outer lumen or tubing of a multi-lumen shaft is inflatable via an inflation pressure by the injected inflation fluid of this invention.

FIG. 3 shows one of the wavy soft shafts 6 under inflation pressure. The curvature of the shaft comes from the pre-shaping of the soft inflatable shaft 6 or outer tubing. In another embodiment, the inflation fluid is injected into the outer lumen in a double-lumen shaft in order to curve the shaft section to conform to the pre-shaped pattern under an inflation pressure. In still another embodiment, the curvature can also come from a steering mechanism at the handle, if so desired. The purpose of the inflation pressure is to keep the shaft resilient and outwardly against the tissue. When higher inflation pressure is applied from an inflation infusion port at the proximal end of the catheter probe system, the shaft 6 shall curve more and conform to the inner contour surface of the heart. By maintaining the electrodes surface round, the major contacting area between a catheter probe system and the tissue is the electrode surfaces 11, rather than the tubing shaft surface 12.

FIG. 4 is a close-up cross-sectional view of the catheter shaft 6 under inflation pressure. The dotted line 13 is the outer surface 12 of the inflatable shaft under no inflation pressure while the solid line 14 is the outer surface 12 of the inflatable shaft under an inflation pressure. The conducting wires 15 are used to transmit the electric signals from the electrodes 10 through a connector to the external ECG monitor. The conducting wires 15 are also used to transmit the radiofrequency energy to the electrodes for therapeutic ablation procedure.

The material of electrodes may include a noble metal or their alloy, such as platinum, iridium, silver or gold. The spacing between the electrodes is in the range of 1 mm to 10 mm, preferably 2 to 5 mm. The material for the inflatable soft shaft is consisted of a non-compliant, a compliant, or a hybrid material.

From the foregoing, it should now be appreciated that an improved catheter probe system has been disclosed herein comprising of a plurality of electrodes on at least one inflatable wavy soft shaft to render a more intimate tissue contact. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter probe system comprising:

a plurality of flexible longitudinally extending shafts each having a distal end, a proximal end, and a lumen extending therebetween;

an inflatable wavy soft shaft section in at least one of the catheter shafts of the catheter probe system, wherein the outer surface of said inflatable wavy soft shaft has a plurality of hills and valleys;

a plurality of conducting electrodes secured on the hills of said inflatable wavy soft shaft;

pressurization means for inflating the inflatable wavy soft shaft, wherein said inflatable wavy soft shaft is pre-shaped to form a generally straight configuration in an uninflated state and to form a curved configuration in an inflated state;

said conducting electrodes individually encircling said inflatable wavy soft shaft and having an outermost circumferential diameter larger than the outer diameter of said at least one catheter shaft;

said valleys having an uninflated geometry wherein the uninflated diameter of the valleys is less than said outermost circumferential diameter of the conducting electrodes; and said valleys further having an inflated geometry wherein the inflated diameter of the valleys is less than said outermost circumferential diameter of the conducting electrodes, but greater than the uninflated diameter of the valleys.

2. A catheter probe system as in claim 1, further comprising the material for the soft shaft being selected from a group consisting of a non-compliant material, a compliant material, or a hybrid material.

* * * * *